United States Patent [19]

Switchenko et al.

[11] Patent Number: 5,563,038

[45] Date of Patent: Oct. 8, 1996

[54] COMPOSITIONS AND METHODS FOR REMOVAL OF DETERGENTS

[75] Inventors: Arthur C. Switchenko, Mountain View; Nurith Kurn, Palo Alto; Christian Neukom, Mountain View; Marcel Pirio; Donald E. Berger, Jr., both of San Jose; Edwin F. Ullman, Atherton, all of Calif.

[73] Assignee: Behringwerke AG, Marburg, Germany

[21] Appl. No.: 154,340

[22] Filed: Nov. 18, 1993

Related U.S. Application Data

[60] Continuation of Ser. No. 879,655, May 6, 1992, abandoned, which is a division of Ser. No. 223,501, Jul. 25, 1988, Pat. No. 5,116,726.

[51] Int. Cl.$^6$ ................................................. G01N 33/531
[52] U.S. Cl. ........................... 435/7.1; 435/961; 435/962; 435/967; 436/543; 510/320; 510/392
[58] Field of Search ..................................... 252/142, 549, 252/550, DIG. 7, DIG. 17, 547, 173, 89, 1, 94, 108, 132; 435/7.1, 961, 962, 967; 436/543

[56] References Cited

U.S. PATENT DOCUMENTS

| | | | |
|---|---|---|---|
| 4,504,409 | 3/1985 | Tsutsumi et al. | 252/351 |
| 4,539,134 | 9/1985 | Martin et al. | 252/156 |
| 4,820,450 | 4/1989 | Wile et al. | 252/545 |

FOREIGN PATENT DOCUMENTS

| | | |
|---|---|---|
| 0167395A2 | 1/1986 | European Pat. Off. |
| 1002881 | 11/1962 | United Kingdom. |

OTHER PUBLICATIONS

Jaeger, et al., Journal of Organic Chemistry, vol 51 (1986), pp. 3956–3959 "Preparation and Characterization of Base--Sensitive Destructible Surfactants".

Jaeger, et al., Journal of Organic Chemistry, vol 49 (1984), pp. 4545–4547, "Destructible Surfactants Based on a Ketal Group".

Jaeger, et al., Joacs, vol 64:11 (Nov. 1987), pp. 1550–1551 "Preparation and Characterization of Souble–Chain Destructible Surfactants and Derived Vesicles".

Jaeger et al., J. Org. Chem. 53, #7, pp 1577–1580 (1988) "Preparation and Characterization of Cleavable Surfactants based on a Silicon–Oxygen Bond".

Chang et al., Chemistry Letters, pp 1385–1388 (Jul. 1987) "Selective Destruction of the Synthetic Vesicles by the Reductive cleavage of Disulfide Linkage".

Livingston et al., J. Am. Oil Chemists'Soc. 42 (8) pp. 720–723 (1965) "The Synthesis and Some Surface Active Properties of Alkylthioalkyl and Alkoxyalkyl Sulfates".

Barnard et al. ,in *Organic Sulfer Compounds*, vol. 1, Ed. by Kharasch, pp. 229–247, Pergamon Press (1961) "Oxidation of Organic Sulfides".

*Primary Examiner*—Lora M. Green
*Attorney, Agent, or Firm*—Theodore J. Leitereg; Rohan Peries

[57] ABSTRACT

Compounds having detergent properties are disclosed. When a modifying reagent is brought into contact with these compounds, the detergent properties are decreased. These compounds are useful, for example, as solubilizing agents for microbial antigens and/or antibodies and for reversibly wetting hydrophobic surfaces. Accordingly, methods are disclosed for increasing the hydrophilic properties of a material, such as a microbial antigen and/or antibody, the methods generally comprising the steps of contacting the material with the compound having detergent properties and a modifiable group, and modifying the compound with a modifying reagent. Kits are also disclosed for use in accordance with this methodology.

12 Claims, No Drawings

5,563,038

COMPOSITIONS AND METHODS FOR REMOVAL OF DETERGENTS

This is a continuation of application Ser. No. 07/879,655 filed May 6, 1992 abandoned, which in turn is a divisional of application Ser. No. 07/223,501 filed Jul. 25, 1988, now U.S. Pat. No. 5,116,726, which issued on May 26, 1992.

BACKGROUND OF THE INVENTION

1. Field of the Invention

Detergents are used throughout industry for a wide range of applications. They not only have home use for cleaning eating ware, floors, clothes, etc., but are used commercially for cleaning manufactured items, in motor fuels, for removal of paints, oil recovery, ore processing, chemical processing, releasing plastic parts from molds, suspension of pigments, insecticides and herbicides, and for use in emulsion polymerization, dissolution of drugs, purification of proteins, bioanalytical applications, etc.

In assays for analytes of interest, it is often necessary to solubilize a microorganism to expose its antigenic sites to recognition by a labelled binding partner. Sometimes a detergent is used to solubilize the microorganism. However, the detergent can interfere with the assay; and, frequently, it is desirable to remove a detergent after it has served its function in assays for microbial analytes. Removal of the detergent generally has some drawbacks. One drawback is that the removal often requires at least one extra processing step. Another drawback is that material is sometimes lost in the extra processing step. Since the micro-organism is present in small quantities, this can be a serious drawback.

Destructible surfactants have been employed in preparative chemistry. Such surfactants have been used to overcome the effects of emulsion formation during extraction procedures in surfactant-based organized media containing micelles, inverse micelles, and microemulsions. After the preparative reaction has taken place, the destructible surfactant is converted to nonsurfactant products under mild conditions.

2. Description of the Related Art

Jaeger, et al. in *J. Org. Chem.* (1986) 51:3956–3959 describe the preparation and characterization of base-sensitive destructible surfactants. Destructible surfactants based on a ketal group are disclosed by Jaeger, et al., *ibid.* (1984) 49:4545–4547. The preparation and characterization of double-chain destructible surfactants and derived vesicles is discussed by Jaeger, et al., *JOACS* (1987) 64(11): 1550–1551.

SUMMARY OF THE INVENTION

According to a first aspect of the invention, a method is disclosed for temporarily increasing the hydrophilic properties of a material. The method comprises: (a) contacting the material in an aqueous medium with a compound having detergent properties (the compound comprising a lipophilic portion, a modifiable group, and a polar portion), whereupon the hydrophilic properties of the material are increased; and (b) modifying the modifiable group with a modifying reagent, whereupon the detergent properties are modified, and the hydrophilic properties of the material reduced. The detergent is a compound having the structural formula L—P, where L is a lipophilic moiety Y—A—Z capable of modification by the modifying reagent, in which:

Y is alkyl, alkenyl, or alkynyl, having from 2 to 12 carbon atoms; or aralkyl, aralkenyl or aralkynyl, having from 7 to 12 carbon atoms;

A is —S—; —Se—; —CHX—, wherein X is Cl, Br, or I; —O—CH=CH—; or —S—S—; and

Z is saturated or unsaturated alkylene having from 1 to 12 carbon atoms or saturated or unsaturated aralkylene having from 7 to 10 carbon atoms;

and P is a hydrophilic moiety.

According to a second aspect of the invention, a method is disclosed for modifying the detergent properties of a detergent in an aqueous medium. This method comprises the step of contacting the medium with a modifying reagent in order to chemically modify the detergent.

According to a third aspect of the invention, an improvement is disclosed in a method for reversibly wetting or dispersing a substance in an aqueous medium, which method comprises contacting the substance with a detergent and removing the detergent. The improvement comprises: (a) employing as the detergent, a compound having the structural formula L—P, wherein L is a lipophilic moiety containing a modifiable group, and P is a hydrophilic moiety; and (b) contacting the combination of the substance and the detergent with a sufficient quantity of a modifying reagent to modify substantially all of the modifiable group of the detergent whereby the detergent loses its detergent properties.

According to a fourth aspect of the invention, a method is disclosed for preparing an analyte for an assay. The method comprises the steps of: (a) solubilizing the analyte with a detergent of the structural formula L—P, wherein L is a lipophilic moiety containing a modifiable group, and P is a hydrophilic moiety; and (b) modifying the properties of the detergent by the addition of a modifying reagent capable of modifying the modifiable group.

According to a fifth aspect of the invention, a kit is disclosed for conducting an assay for determining an analyte in a sample suspected of containing the analyte. The kit comprises, in packaged form:

a compound having detergent properties and having the structural formula Y—A—Z—P, wherein:

wherein Y is alkyl, alkenyl, or alkynyl, having from 2 to 12 carbon atoms; or aralkyl, aralkenyl or aralkynyl, having from 7 to 12 carbon atoms;

A is —S—; —Se—; —CHX—, —CH(X)CH=CH—, wherein X is Cl, Br, or I; —O—CH=CH—; —S—S—; —SO$_2$CH$_2$CH$_2$O—; a ketal group; or —Si(R)$_2$O— and —OSi(R)$_2$O— wherein R is lower alkyl;

Z is saturated or unsaturated alkylene having from 1 to 12 carbon atoms or saturated or unsaturated aralkylene having from 7 to 10 carbon atoms; and P is a hydrophilic moiety; and a modifying reagent capable of modifying the detergent properties of the compound Y—A—Z—P.

According to a sixth aspect of the invention, a kit is disclosed for conducting an assay for determining an analyte in a sample suspected of containing the analyte, the analyte being a member of a specific binding pair consisting of a ligand and its complementary receptor. The kit comprises in packaged form:

(1) a detergent having the structural formula Y—A—Z—P, wherein:

wherein Y is alkyl, alkenyl, or alkynyl, having from 2 to 12 carbon atoms; or aralkyl, aralkenyl or aralkynyl, having from 7 to 12 carbon atoms;

A is —S—; —Se—; —CHX—, —CH(X)CH=CH—,
wherein X is Cl, Br, or I; —O—CH=CH—;
—S—S—; SO$_2$CH$_2$CH$_2$O—;

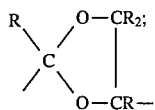

or —Si(R)$_2$O—, —OSi(R)$_2$O— wherein R is independently H or lower alkyl;

Z is saturated or unsaturated alkylene having from 1 to 12 carbon atoms or saturated or unsaturated aralkylene having from 7 to 12 carbon atoms; and P is OSO$_3$H, SO$_3$H, COOH, PO(OR)OH, or OPO(OR)OH, wherein R is H or lower alkyl; and (2) a member of the specific binding pair complementary to the analyte.

According to a seventh aspect of the invention, a composition is disclosed. The composition includes an aqueous medium containing a microbial antigen and/or its complementary antibody, and a compound of the formula Y—A—Z—P, wherein:

Y is alkyl, alkenyl, or alkynyl, having from 2 to 12 carbon atoms; or aralkyl, aralkenyl or aralkynyl, having from 7 to 12 carbon atoms;

A is —S—; —Se—; —CHX—, —CH(X)CH=CH—, wherein X is Cl, Br, or I; —O—CH=CH—; —S—S—; —SO$_2$CH$_2$CH$_2$O; a ketal group; or —Si(R)$_2$O—, —OSi(R)$_2$O— wherein R is lower alkyl;

Z is saturated or unsaturated alkylene having from 1 to 12 carbon atoms or saturated or unsaturated aralkylene having from 7 to 12 carbon atoms; and P is a hydrophilic moiety.

According to an eighth aspect of the invention, a compound is disclosed having the formula CH$_3$(CH$_2$)$_n$—S—(CH$_2$)$_m$OW, wherein n is an integer of 2 to 4, m is an integer of 6 to 11 and W is H or SO$_3$H.

According to a ninth aspect of the invention, a compound is disclosed having the formula CH$_3$(CH$_2$)$_q$—S—CH=CH—(CH$_2$)$_p$OW wherein q and p are independently 2 to 10 and W is H or SO$_3$H.

DESCRIPTION OF THE SPECIFIC EMBODIMENTS

The present invention provides a method of chemically changing the properties of a detergent in order to more efficiently remove it or eliminate the need for removal. Before proceeding further with a description of the invention, the following terms are defined.

Alkyl, alkenyl, alkynyl, aralkyl, aralkenyl, and aralkynyl all refer to hydrocarbon chain radicals having a specified number of carbon atoms, up to four carbon atoms if the term "lower" precedes the radical name, or if there is no specification of chain length, having up to 12 carbon atoms:

Accordingly, alkyl means a branched or unbranched saturated hydrocarbon radical such as methyl, ethyl, n-propyl, isopropyl, n-butyl, iso-butyl, sec-butyl, tert-butyl, pentyl, hexyl, heptyl, octyl, nonyl, decyl, undecyl, dodecyl, etc., including positional isomers.

Alkenyl refers to any branched or unbranched unsaturated carbon chain radical having the number of carbon atoms specified, or up to 12 carbon atoms if no limitation on the number of carbon atoms is specified. Accordingly, alkenyl radicals have 1 or more double bonds between carbon atoms, e.g., vinyl, allyl, 1-propenyl, 2-butenyl, 1,3-butadienyl, 2-pentenyl, etc., and are otherwise of similar scope to alkyl radicals, defined above.

Alkynyl refers to hydrocarbon radicals of the scope of alkenyl, but having 1 or more triple bonds in the radical, e.g., ethynyl, 2-propynyl, 2-penten-4-ynyl, etc.

Aralkyl of 7 to 12 carbon atoms refers to a radical having an alkyl group to which is attached a benzene ring, such as the benzyl radical, phenethyl radical, 3-phenylpropyl radical, an the like.

Aralkenyl and aralkynyl are of similar scope, except that an alkenyl or alkynyl group replaces the alkyl group to which the benzene ring is attached. Examples of aralkenyl and aralkynyl are styryl and benzylidyne, respectively.

Saturated or unsaturated alkylene having from 1 to 12 carbon atoms means, for the purposes of this invention, a hydrocarbon chain (a radical) that is part of a molecule (in this context, part of a detergent or compound having detergent properties), and that is situated such that it bridges two other parts of the molecule. Specifically, in the formula Y—A—Z—P described herein, Z can be alkylene, such as methylene (—CH$_2$—), ethylene (—CH$_2$—CH$_2$—), and the like. For the purposes of this invention, however, the term alkylene is used for corresponding unsaturated radicals, such that —CH=CH— for example, would be understood to be within the scope of "unsaturated alkylene." Similarly, saturated or unsaturated aralkylene is a carbon chain having a benzene ring as a side chain in place of a hydrogen atom, such that —CH(C$_6$H$_5$)— would be an example of saturated aralkylene.

An analyte is a compound or composition to be measured, which is usually a specific binding pair member (defined below) and may be a ligand or a receptor.

An antigen is any substance to which an organism can elicit an immune response. Antigens are generally capable of binding specifically to complementary antibodies. Antigens may be any organic group and will normally be poly(amino acids), i.e., polypeptides and proteins, polysaccharides, lipopolysaccharides, glycoproteins, lipoproteins, ribonuclear proteins, and the like. The antigens will frequently be components of bacteria, viruses, mitochondria, nuclei, cell membranes and the like. In this context:

Polysaccharides are a combination of at least about three or four monosaccharides, linked together by glycosidic bonds. Polysaccharides include, for example, starch glycogen, cellulose and dextran.

A wide variety of proteins may be considered: the family of proteins having similar structural features, proteins having particular biological functions, proteins related to specific microorganisms, particularly disease causing microorganisms, etc.

Lipopolysaccharides (LPS) are molecules containing lipid and polysaccharide moieties and are present in the outer layer of the cell membranes of gram-negative bacteria.

Bacteria include gram-negative bacteria, including but not limited to, *Chlamydia trachomatis, Chlamydia psittaci, E. coli, Pseudonoms fluorescens, Azotobacter vinelandii, Proteus vulgaris, Hydrogenomanas sp., Aerobacter aerogenes, Nisseria gonorrhoeae, Treponema pallidum, Serratia marcescens, Achromobacter fischer, Bacillus subtills, Bacillus megaterium, Sarcina lutea, Micrococcus pyogenes, Lactobacillus casei, Torulopsis utilis* and *Streptomyces griseus*, Shigella, Campylobacter, Salmonella, Legionella, *Hemophillus influenza*, and so forth.

A microbial antigen is an antigen that is present in a host that is in a disease state, where the disease is caused by a microbe such as a bacteria (examples of such diseases are gonorrhea and chlamydia).

For the most part, the antigens employed in the subject invention will have a molecular weight of at least about 1,000, more usually at least about 2,500, frequently greater than 5,000. In the poly(amino acid) category, the poly(amino acids) of interest will generally be from about 5,000 to 5,000,000 molecular weight, more usually from about 20,000 to 1,000,000 molecular weight. The precise nature of some of the antigens together with numerous examples thereof are disclosed in U.S. Pat. No. 4,299,916 to Litman, et al., particularly at columns 16 to 23, the disclosure of which is incorporated herein by reference.

An antibody is a molecule, i.e., an immunoglobulin, formed by the immune system of a host in response to exposure to an antigen. Generally, an antibody specifically binds to, and is accordingly defined as complementary to, the antigen. The antibody can be monoclonal or polyclonal and can be prepared by techniques that are well known in the art such as immunization of a host and collection of sera (polyclonal) or by preparing continuous hybrid cell lines and collecting the secreted protein (monoclonal). Antibodies may include a complete immunoglobulin or fragment thereof, which immunoglobulins include the various classes and isotypes, such as IgA, IgD, IgE, IgGl, IgG2a, IgG2b and IgG3, IgM, IgGl, IgG2, IgG3, IgG4 etc. Fragments thereof may include Fab, Fv and F(ab')$_2$, Fab', and the like. When it is recited herein that a solution or material comprises an antigen or an antibody, the solution or material can comprise both the recited antigen and the recited antibody.

An assay kit is a product, having reagents in packaged combination, used to determine the presence of an analyte in a sample. The reagents are packaged to insure shelf-life, for example, each in separate containers in instances where co-reactivity would destroy shelf life if the reagents were packaged together.

A detergent, or a compound having detergent properties, refers to a compound that can, upon contact with another material, change the hydrophilic properties of that other material. Generally, a detergent increases these hydrophilic properties. Accordingly, a detergent or a compound having detergent properties increases the contacted material's ability to absorb or adsorb water. The detergents according to this invention have a hydrophilic moiety, such as an acidic group or a salt thereof, a lipophilic moiety, and a modifiable group. The modifiable group has an "unnmodified state" and a "modified state". In the unmodified state, the detergent or compound having detergent properties has the effect of increasing the hydrophilic properties of the material with which it is in contact. In the modified state, the detergent properties are decreased, such that the hydrophilic properties of the contacted material are reduced.

A modifying reagent is a reagent that chemically modifies the detergent, or the compound having detergent properties, thereby changing the modifiable group from the unmodified to the modified state. There are several ways that the modifying reagent can act upon the modifiable group in the detergent:

For example, the modifying reagent can act by cleaving the detergent at or near the modifiable group. For the purposes of this invention, "cleaving" means splitting the detergent molecule at one or more bonds of any type (accordingly, the term is to be broadly construed, to include dissociation into one or more fragments). Examples of nucleophilic modifying reagents that can cleave or add to the detergent at a modifiable group are: fluoride, thiourea (i.e., $NH_2$—CS—$NH_2$); hydroxylamine ($NH_2OH$); hydrazines (i.e., compounds containing the R—NH—$NH_2$ group, where R is hydrogen or alkyl of 1 to 4 carbon atoms); hydrazides (i.e., R—CO—NH—$NH_2$ where R is alkyl of 1 to 4 carbon atoms); ammonia; mercaptans (lower alkanethiols), such as ethyl mercaptan (ethanethiol: $CH_3CH_2SH$); mercapto alcohols such as dithioerythritol and mercapto acids such as HS—R—COOH where R is alkyl up to 4 carbon atoms; thiosulfates (i.e., $M_2(S_2O_3^=)_n$ where M is a cation with n positive charges); and thioacids (i.e., R—CO—SH, R—CS—OH or R—CS—SH where R is alkyl of 1 to 4 carbon atoms). The foregoing nucleophilic reagents could, for example, cleave silylethers, disulfides, esters, ketones or Schiff bases, or enter into nucleophilic substitution reactions such as, for example, displacement of halides in alkyl halides, allylic halides, or 3-haloalkynes, typically allylic chlorides. The modifying reagent can be an anion selected from the group consisting of anions containing sulfur such as sulfide, etc., oxygen such as hydroxide, alkoxide, aralkoxide, etc., or nitrogen such as azide, ammonia, etc.

Additionally, the modifying reagent can act by oxidizing the modifiable group. Suitable oxidants are hypochlorite and hypobromite. Additionally, peroxides and peracids are good oxidizing agents, such as lower alkyl or acyl hydroperoxides, perborate, persulfate, and peracetate. Such oxidizing reagents could oxidize many types of modifiable groups, such as seleno or thioethers, seleno or thio vinyl ethers, sulfoxides, or enolethers.

Yet another mode of action for a modifying agent is by reducing the modifiable group. Suitable reducing agents are sulfite salts, hyposulfite salts, and mercaptans, particularly C3 and C4-bis mercapto alkanes and alkanols which can reduce disulfide bonds.

A specific binding pair (sbp) consists of two different molecules (first and second sbp members), where one of the molecules has an area on the surface or in a cavity which specifically binds to a particular spatial and polar organization of the other molecule. The two members of a specific binding pair are referred to as a ligand and its complementary receptor (antiligand).

The present invention is generally directed to a method for removal of detergents by chemically modifying the detergent to modify or destroy its detergent properties. Usually the method will be useful for detergents used in an aqueous medium. The method uses modifying reagents which will not damage the material to be freed of detergent, and which yield more than mere protonation or deprotonation of the detergent. Reducing agents and changes in pH can be used. Usually a mild oxidant or a nucleophile is used. Preferred oxidants are peroxides and peracids. Preferred nucleophiles are thiosulfates, mercaptoacids, thiourea, hydroxylamines, ammonia, hydrazines, hydrazides, etc. Preferred reducing agents are dithioerythritol, dithiothreitol, ascorbic acid, borohydride, etc.

Detergents are used that, on reaction with these modifying reagents, markedly change in polarity or are cleaved. Normally a nonpolar modifiable group that enhances or does not eliminate the detergent properties is incorporated into a detergent. The modifiable group will preferably be located to maximally interfere with the detergent properties when it is modified. This group will normally be situated in the lipophilic portion of the detergent, preferably near the center of the lipophilic portion or distal from the center and the hydrophilic group or, if more than one group is used, spaced to provide segments of greatly reduced lipophilic properties.

Accordingly, a typical formula for a detergent used in this invention would be L—P, where L is a lipohilic moiety containing a modifiable group, and P is a hydrophilic moiety. Preferably, the lipophilic moiety has the formula Y—A—Z. In this formula, Y is a saturated or unsaturated aliphatic hydrocarbon having from 2 to 12 carbon atoms, or is aralkyl, aralkenyl or aralkynyl of up to 12 carbon atoms. A is a modifiable group, such as —S—; —Se—; —CHX— or —CHX—CH=CH— where X is Cl, Br, or I; —O—CH=CH—; or —S—S—. Z is saturated or unsaturated alkylene having from 1 to 12 carbon atoms or saturated or unsaturated aralkylene having from 6 to 10 carbon atoms. Preferably, Z has from 2 to 10 carbon atoms, especially when A is not —O—CH=CH— (the latter A already provides 2 carbon atoms). P is preferably $OSO_3H$, $SO_3H$, COOH, PO(OR)OH, or OPO(OR)OH, wherein R is H or lower alkyl.

The detergent must be capable of chemical modification upon addition of a modifying reagent. There are many ways of carrying out such a chemical modification, including, but not limited to, cleaving, oxidizing, and reducing the modifiable group. Cleaving can be accomplished, for example, with the use of a nucleophile, such as a fluoride, a thiosulfate, a mercaptan, a thioacid, a thiourea, a hydroxylamine, a hydrazine, a hydrazide or ammonia. Oxidizing can be accomplished, for example, with a peroxide or a peracid such as a lower alkyl or acyl hydroperoxide, $H_2O_2$, perborate or persulfate; or by using hypochlorite or hypobromite. Reducing can be accomplished, for example, by using a sulfite salt, a hyposulfite salt, or a lower alkyl or lower acyl mercaptan.

Of course, the modifiable group must be one that can be acted upon by the modifying reagent. For example, when an acid is used as a modifying reagent to disrupt the detergent, the modifiable group can be an enolether or acetal. Alternatively, the modifiable group can be a Schiff base or enamine.

When a reducing agent is used as a modifying reagent, such as a mercaptan, the modifiable group can be a disulfide.

When a nucleophile is used as a modifying reagent, the modifiable group can be a Schiff base or ketone, but will preferably be chloride, bromide, or iodide, preferably an allylic halide or a 3-haloalkyne, usually an allylic chloride or, when the nucleophile is fluoride, the modifiable group may be a silyl ether.

When an oxidant is used as a modifying reagent, the modifiable group can be a seleno or thio ether or a seleno or thio vinyl ether.

Preferred applications of this invention are for bioanalytical and drug delivery technology. For drug delivery, emulents can be provided that will release a drug by contact with a releasing agent, and liposomes used in drug delivery can be freed of contaminating detergents. For bioanalytic use, latex particles prepared by emulsion polymerization can be freed of detergent. Proteins can be recovered from detergent solutions used in gel electrophoresis. Cell membrane components that are separated by solubilization with detergents can be reconstituted. Antigens can be separated from cellular debris and biological fluids by detergents and then freed of the detergent to permit adsorption on surfaces and/or antibody binding.

The method has particular application to analytical microbiology. Microbial antigens, particularly chlamydia lipopolysaccharide, and gonococcus surface proteins can be solubilized by detergent of the present invention and then released so as to permit analysis by antibody binding. For this purpose, derivatives of alkylsulfate detergents are preferred, having the formula:

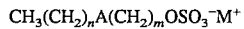

where A can be, for example, —S—, —S—S—, —S—CH=CH—, —Se—, —Se—CH=CH—, —CHX—, —CH(X)CH=CH— (X=Cl, Br, I), —O—CH=CH—; —SO$_2$CH$_2$CH$_2$O—; —Si(R)$_2$O—, —OSi(R)$_2$O—, wherein R is lower alkyl; n and m can vary from 1 to 12, and together are at least 5; and M is an alkali metal. More preferably, however, A is —S—; —Se—; —CHX—, wherein X is Cl, Br, or I; —O—CH=CH—; or —S—S—. Most preferably, A is —S—, n is an integer of 1 to 6, and m is and integer of 4 to 11.

Particularly preferred detergents are:

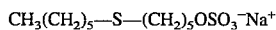

Detergent I

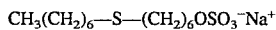

Detergent II

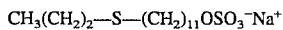

Detergent III

Of these, Detergent II is presently the most preferred. These compounds can solublize antigen and then release the antigen when treated with hydrogen peroxide.

The present invention has application to numerous techniques known for detecting antigens in a sample, such as a biological fluid, i.e., blood, urine, cell cultures. It is important to be able to quickly and accurately detect the presence of antigens such as gram-negative bacteria, i.e., *Chlamydia trachomatis, Chlamydia psittaci* and *Neisseria gonorrhoeae* because of the prevalence of diseases associated with such bacteria. Some of the techniques utilized to detect antigens involve cell culture procedures, electrophoresis, and the like.

Many of the detection techniques involve immunoassays. Some of these techniques involve detecting antibodies to the antigen of interest. It is, however, preferable to assay for antigens rather than antibodies. Immunoassay techniques for the detection of antigens often involve enzyme immunoassays such as the enzyme linked immunosorbent assay generally referred to as ELISA. Such assays typically involve detecting the antigen of interest by coating the antigen on a bare solid surface or a surface that has been pre-coated with a protein such as an antibody. After coating the surface of the support with the antigen, the surface is washed to remove unbound antigen. Thereafter, the antigen on the surface is contacted with antibody for the antigen that is labeled or is capable of being labeled. The surface is again washed and the antibody that has bound to the surface of the support is detected by detecting the label.

One method for determining *Chlamydia trachomatis* antigen in a clinical specimen is disclosed in U.S. Pat. No. 4,497,899. The method disclosed involves lysing Chlamydia cells in the specimen to release the antigen; coating a bare solid support with the cell lysate; separating the coated support from the specimen; treating the separated support with antibody to form an antigen-chlamydia antibody complex on the support; separating the complex from unbound antibody; treating the bound complex with labeled antiglobulin to form an antigen-antibody-labeled antiglobulin complex on the support; separating the latter complex from unbound labeled antiglobulin; and determining bound labeled antiglobulin as a measure of antigen in the specimen. U.S. Pat. No. 4,497,900 discloses a method for determining *Neisseria gonorrhoeae* analagous to that in U.S. Pat. No. 4,497,899.

An indirect method for determining an antigen in a liquid sample is disclosed in U.S. Pat. No. 4,067,959 involving adsorbing antigen of the same immunological type as the sample antigen onto a solid support surface, reacting a known quantity of specific labeled antibody in solution with the sample antigen and with the adsorbed antigen. The labeled antibody is in excess so that a portion of the labeled antibody is bound in the solution to the sample antigen and excess labeled antibody immunologically reacts with the adsorbed antigen on the surface. The surface is washed and then the quantity of reacted labeled antibody on the surface is determined as a measure of the antigen in the sample.

A method for assaying for the presence of a Chlamydial infection involving generating antibodies against the principal outer membrane protein of *Chlamydia trachomatis* is disclosed in U.S. Pat. No. 4,427,782. The method comprises treating a sample suspected of containing chlamydial infection to solubilize the Chlamydia outer cell membrane protein, contacting the generated antibodies with the solubilized specimen and determining the reaction between the antibodies and the solubilized specimen.

Another method for detecting an antigen in a biological sample is disclosed in U.S. patent application Ser. No. 135,869, filed Dec. 21, 1987. The method involves providing in combination a solid support, which is substantially free of specific binding proteins, and a medium comprising an antigen from the sample and an antibody for the antigen. The combination is incubated under conditions sufficient for the antibody when bound to the antigen to bind to the support. The presence or amount of antibody on the support or in the medium is determined and is related to the presence of antigen in the sample.

The disclosures of the above patents and patent applications are incorporated herein by reference in their entirety. In many of the above methods solubilization of a microorganism is important or necessary.

Solubilization thereof can be accomplished in accordance with the present invention by incubation of the bacterial sample in the presence of a detergent as described above, usually in the concentration range of from about 0.01 to 1.0%, weight to volume. Temperatures employed for solubilizing the bacterial sample are usually in the range from about 10° to 50° C., more usually from about 15° to 100° C. For the most part, relatively short times are required for solubilization. Usually, the solubilization can take at least about 5 seconds and not more than 1 hour, more usually about 30 seconds to about 30 minutes. The time is dependent on the nature of the bacterial sample, the antigen, and the type and amount of detergent and temperature used.

The solubilization medium is generally aqueous and may contain up to 40% of an organic solvent. The pH of the solubilization medium will usually be in the range of about 2 to 12, more usually in the range of about 5 to 9. The pH is generally chosen to achieve a high level of solubilization of the antigen. Various buffers may be used to achieve and maintain the pH during the solubilization. Illustrative buffers include borate, phosphate, carbonate, Tris, barbital and the like. The particular buffer employed is not critical but one buffer may be preferred over another.

In immunoassays where solid-phase surfaces are employed for the capture of solubilized bacterial components (antigen) and a known detergent such as SDS, Triton, NP-40, sarcosyl, or chenodeoxycholate is used for the solubilization, sample dilution is usually required subsequent to the solubilization step in order to reduce the interference of the detergent on the binding of antigen to the captive surface. The present invention substantially reduces the need for or avoids such a dilution and thereby provides for greater assay sensitivity.

Thioether compounds (A=—S—) for use in the methods, kits, and compositions of the present method can be prepared, for example, by reacting an appropriate thiol with a haloalcohol under conditions for displacement of the halide by deprotonated thiol to yield a thioether alkanol, which can then be converted to an ester comprising the hydrophilic moiety.

For example, referring to Scheme I:

SCHEME I

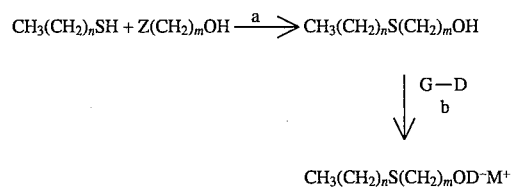

wherein:

n and m can vary from 1 to 12;

Z=Cl or Br;

G=Cl, Br, or Y, where Y=(CH$_3$CH$_2$)N, (CH$_3$)$_3$N, or pyridine;

D=SO$_3$, PO(OR)O, wherein R is H or lower alkyl, ClC(O)NHCH$_2$ SO$_3$, or ClC(O)CH$_2$CH$_2$COD M=Na or K a=metal hydride such as sodium hydride in an ether solvent such as ethyl ether, tetrahydrofuran, etc.; and b=aqueous alkali such as sodium hydroxide, potassium hydroxide, etc.

Modifiable detergents containing a selenium group (A=—Se—) for use in the present invention can be prepared in a manner similar to that described above for the destructible detergents containing a thioether linkage.

Vinyl thioether detergents (A=—S—CH=CH—) for use in the method, kits, and compositions of the present invention can be prepared, for example, by reacting an appropriate thiol with an appropriate alkynyl alkanol under conditions wherein the thiol moiety adds to the alkynyl group. The resulting vinyl thioether alkanol is then converted to an ester comprising the hydrophilic moiety. For example, referring to Scheme II:

SCHEME II

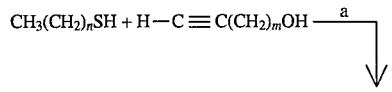

-continued
SCHEME II

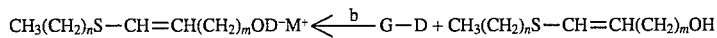

wherein:
n and m can vary from 1 to 12;
M=Na or K;
G=Cl or Br or Y, wherein Y=$(CH_3CH_3)_3N$, $(CH_3)_3N$, or pyridine;
D=$SO_3$, PO(OR)O wherein R is H or lower alkyl, ClC(O)NHCH$_2$CH$_2$SO$_3$, ClC(O)CH$_2$CH$_2$COO, etc.;
a=diacyl peroxide such as dibenzoyl peroxide, etc. in an alkane ($C_5$–$C_8$) solvent such as heptane, etc.; and
b=aqueous alkali such as sodium hydroxide, potassium hydroxide, etc.

Disulfide detergents (A=—S—S—) for use in the present invention can be prepared, for example, by reacting an appropriate thiol with an appropriate activated halosulfide under conditions for displacement of the activating group by the thiol group to form an activated disulfide, which can be reacted with an appropriate thiol alkanol. The resulting disulfide alkanol can then be treated to convert the alcohol moiety to an ester comprising the hydrophilic moiety. For example, referring to Scheme III:

SCHEME III

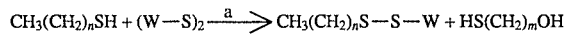

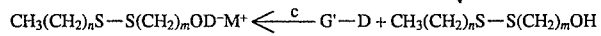

wherein:
n and m can vary from 1 to 12;
G'=Br, Cl, or Y where Y=

NO$_2$—C$_6$H$_4$S—, 2-pyridylthio, etc.;

D=$SO_3$, PO(OR)O where R is H or lower alkyl, ClC(O)NHCH$_2$CH$_2$SO$_3$, ClC(O)CH$_2$CH$_2$COO, etc.;
M=K or Na;

W=

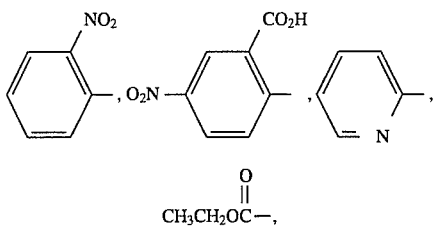

etc.;
a=tri(lower)alkylamine, such as triethylamine in ether such as ethyl ether, tetrahydrofuran, etc.;
b=a; and
c=aqueous alkali such as sodium or potassium hydroxide, etc.

Vinyl ether detergents (A=—O—CH=CH—) for use in the methods, kits, and compositions of the present invention can be prepared, for example, by reaction of an appropriate alkanol with an appropriate tri(lower)alkyl silylated alcohol aldehyde and a diazomethyl lower alkyl phosphate under strongly basic conditions to give a vinyl ether with a terminal silyl group, which can be converted to an ester comprising the hydrophilic moiety. For example, referring to Scheme IV:

SCHEME IV

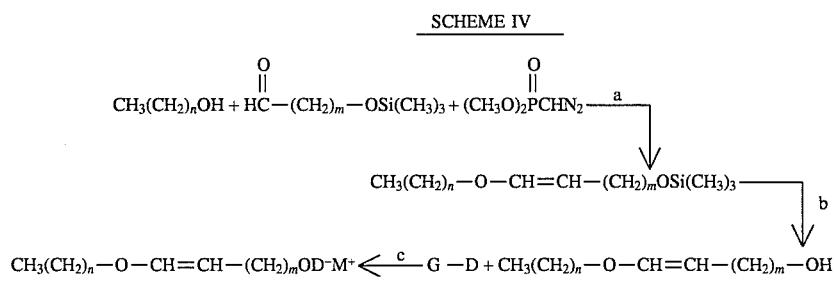

wherein:
n and m can vary from 1 to 12;
G=Cl, Br, or Y where Y=$(CH_3CH_2)_3N$, $(CH_3)_3N$, or pyridine;

D=$SO_3$, PO(OR)O where R=H or lower alkyl, ClC(O)NHCH$_2$CH$_2$SO$_3$, ClC(O)CH$_2$CH$_2$COO, etc.;

M=Na or K;

a=metal salt of lower alkyl alcohol, such as tert-butyl alcohol, etc.;

b=metal halide such as sodium fluoride, etc.; and c=aqueous alkali such as sodium or potassium hydroxide, etc.

Haloalkyl detergents (A=—CHX—) for use in the present invention can be prepared from the corresponding alkenyl alcohol by reaction with a haloacid. The alcohol moiety of the resulting haloalkyl alkanol is then converted to a hydrophilic moiety. For example, referring to Scheme V:

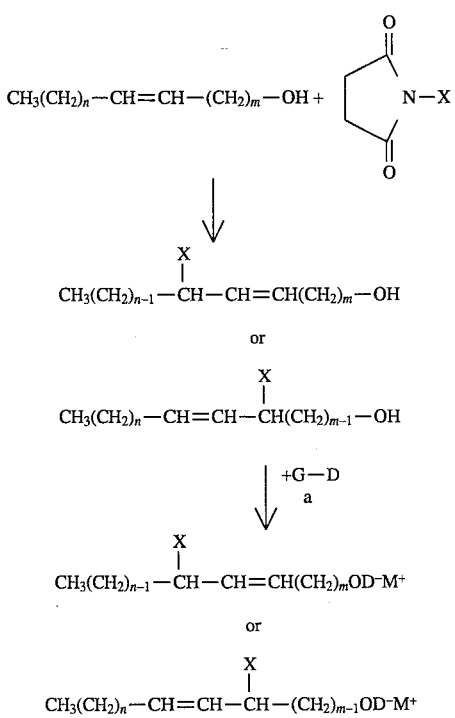

wherein:

n and m can vary from 1 to 12;

X=Cl, Br, or I;

G=Cl, Br, or Y where Y=(CH$_3$CH$_2$)$_3$N, (CH$_3$)$_3$N, or pyridine;

D=$SO_3$, PO(OR)O wherein R is H or lower alkyl ClC(O)NHCH$_2$CH$_2$SO$_3$, or ClC(O)CH$_2$CH$_2$COO; and M=K or Na;

a=aqueous alkali such as sodium or potassium hydroxide, etc.

Modifiable detergents containing a selenium group (A=—Se—) for use in the present invention can also be prepared by reacting a symmetrical dialkyl diselenide with a metal trialkylborohydride in an ether solvent to give a alkyl metal selenolate, which can be reacted with an appropriate haloalcohol. The alcohol moiety of the resulting seleno-alkanol can then be esterified with the appropriate hydrophilic moiety. For example, referring to Scheme VI:

SCHEME VI

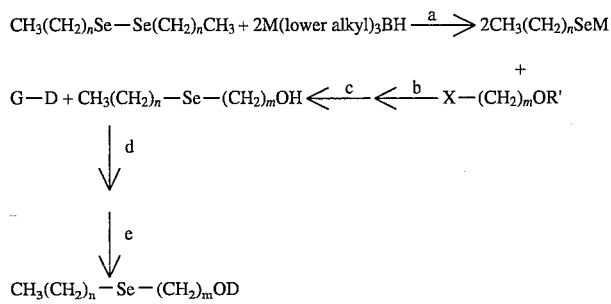

wherein:

n and m can vary from 1 to 12;

M=a metal such as lithium, etc.;

R'=alcohol protecting group such as (CH$_3$)$_3$Si—, etc.;

G=Cl, Br, or Y where Y=(CH$_3$CH$_2$)$_3$N, (CH$_3$)$_3$N or pyridine;

D=SO$_3$H, PO(OR)OH, where R is H or lower alkyl ClC(O)NHCH$_2$CH$_2$SO$_3$H, ClC(O)CH$_2$CH$_2$COOH;

a=ether solvent such as ethyl ether, tetrahydrofuran, etc.;

b=same as a;

c=agent for removing a protecting group from an alcohol, such as (CH$_3$)$_4$N$^+$F$^-$, etc.;

d=aqueous alkali, such as sodium or potassium hydroxide, etc.; and e=aqueous and such as hydrochloric and sulfuric acid, etc.

All of the above compounds can be prepared as a metal salt of the hydrophilic group such as the sodium salt, potassium salt and the like.

Other detergents (A=—SO$_2$CH$_2$CH$_2$O—, a ketal group, or —Si(R)$_2$O— wherein R is lower alkyl) for use in the assay methods, kits, and compositions of the present invention can be prepared according to procedures described by Jaeger, et al., supra.

As mentioned above, the modifying reagent and conditions chosen for modifying the properties of a detergent used in accordance with the present invention vary depending on the particular modifying group. The following reagents and conditions are provided by way of example and not limitation.

Nucleophilic modifying reagents and conditions:

(a) β-mercaptoethanol at alkaline pH for disulfide cleavage, (b) thioacetic acid, (c) hydroxylamine at alkaline pH, (d) hydrazine at alkaline pH, (e) ammonia at alkaline pH, and (f) thiourea at alkaline pH.

Oxidizing modifying agents and conditions:

(a) hydrogen peroxide in acetate buffer, pH 4.5, (b) sodium periodate in water, (c) peracetic acid in acetic acid,

15

(d) dichlorophenyl iodide in an organic solvent, (e) tert-butoxy hydrochlorite in water, (f) sodium hypochlorite or hypobromite in water, (g) perborate, sodium borate at alkaline pH, and (h) $Na_2S_2O_8$ in water.

Reductive modifying reagents and conditions:

(a) dithiothreitol or dithioerythritol, pH 8 for reductive cleavage of disulfides, (b) tripbenylphosphine in aqueous dioxane, (c) n-butylphosphine at alkaline pH, and (d) sodium sulfite at alkaline pH.

EXAMPLES

The invention is further demonstrated by the following illustrative examples. Parts and percentages are by weight to volume except where otherwise indicated.

Example I

Preparation of Degradable Detergent Containing Thioether Group

Part A:

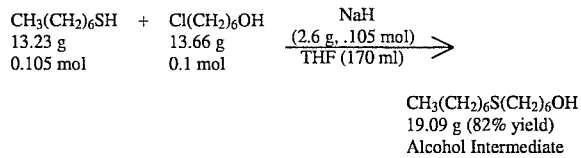

$CH_3(CH_2)_6S(CH_2)_6OH$
19.09 g (82% yield)
Alcohol Intermediate

1. Heptyl mercaptan in tetrahydrofuran (THF) was added to a vigorously stirred suspension of NaH in THF over 45 minutes. The mixture was stirred at room temperature for one hour under argon.
2. Chlorohexanol in THF was added dropwise to a vigorously stirred suspension of sodium heptyl mercaptide under argon over 30–45 minutes. The mixture was stirred at room temperature under argon for 24 hours. Reaction completion was checked by thin layer chromatography.
3. The THF was evaporated on a rotary evaporator. Water was added, and extraction was performed three times with ethyl acetate (EtOAc). The EtOAc extraction was washed with water. Then the EtOAc extracts were washed with saturated brine, and dried over $Na_2SO_4$. The $Na_2SO_4$ was filtered and evaporated to a yellow oil on a rotary evaporator.
4. The product was chromatographed with a Waters Prep 500 HPLC, using hexane-EtOAc. Appropriate fractions were combined and evaporated to a clear, light yellow oil. The product was distilled under vacuum, boiling point 85°–100° C./0.01 mm.

Part B:

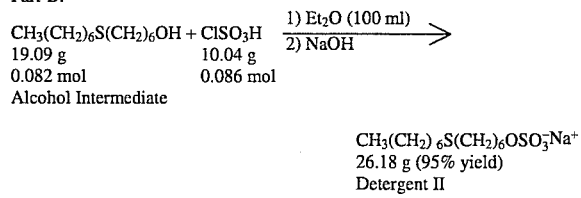

$CH_3(CH_2)_6S(CH_2)_6OSO_3^-Na^+$
26.18 g (95% yield)
Detergent II

1. The $Et_2O$ (ethyl ether) was cooled to 0°–5° C. with stirring under argon.
2. $ClSO_3H$ was added dropwise, maintaining temperature at 0°–5° C.
3. The Alcohol Intermediate was added dropwise, maintaining temperature at 0°–5° C.

16

4. $Et_2O$ was removed on rotary evaporator; then $Et_2O$ was added and evaporated again on a rotary evaporator/vacuum pump.
5. The solution was poured slowly into an NaOH/ice solution. The pH was adjusted to 10.
6. An extraction was made with petroleum ether. Ethanol was added to assist in phase separation and defoaming.
7. Product was dried by rotary evaporation followed by lyophilization.

Example II

This Example illustrates the use of a chemically-modifiable thioether detergent in the assay for *Neisseria gonorrhoeae*, and compares the performance of the modifiable detergent to that of sodium dodecyl sulfate (SDS), using nitrocellulose for non-specific capture of antigen and rabbit polyclonal antibodies for antigen detection.

Protocol

1. Antigen (Ag) Solubilization—*N. gonorrhoeae* (GC) was solubilized ($5\times10^6$ cells/ml) in solubilization buffer consisting of:

Solubilization Buffer A=0.5% Detergent I ($Na^+O^-_3SO(CH_2)_5S(CH_2)_5CH_3$) in 0.1M Acetate (pH 4.6) containing 0.1M NaCl.

Solubilization Buffer B=0.5% SDS ($Na^+O^-_3SO(CH_2)_{11}CH_3$) in 0.1M Acetate (pH 4.6) containing 0.1M NaCl.

The solutions were incubated at room temperature for 15 minutes to promote solubilization of gonococcal cell surface components (Ag) and then further diluted 100 fold with the same buffers or with a detergent free buffer consisting of 0.1M acetate and 0.1M NaCl, pH 4.6. Controls consisted of the buffers alone without cells added.

2. Oxidation—To 0.5 ml of each of the solutions prepared from detergent containing buffer was added sufficient $H_2O_2$ (30%) to yield a final concentration of 1% after which the solution was incubated at room temperature for 15 minutes.

3. Assay Procedure

A. Aliquots (0.1 ml) of each solution were applied in duplicate to a nitrocellulose filter (0.8μ pore size) mounted on an absorbent paper pad.

B. 0.1 ml Standard Diluent (80% fetal bovine serum, 15% glycerol, 4.9% 0.2M Tris (pH 7.5), and 0.1% Tween 20) was applied to the nitrocellulose filter to reduce non-specific binding of the remaining reagents.

C. 0.05 ml 1% whole Rabbit Anti-GC antiserum (in standard diluent) was then applied and allowed to incubate with the filter at room temperature for 5 minutes.

D. Washing was carried out by applying 0.1 ml of Standard Diluent to the filter.

E. 0.05 ml 1 μg/ml Horseradish peroxidase (HRP)-labeled goat anti-rabbit IgG (Heavy plus light chains) in Standard Diluent was applied and allowed to incubate with the filter at room temperature for 5 minutes.

F. Washing was carried out by applying 0.1 ml of Standard Diluent followed by 0.1 ml of 0.1M citrate, pH 5.5.

G. 0.05 ml of a buffered solution comprising dicarboxidine and $H_2O_2$, pH 5.0, was applied and incubation was carried out at room temperature for 8 minutes.

H. Reactions were stopped by addition of 0.1 mL of 0.1M citrate, pH 5.5.

I. Color intensity of the filter was recorded.

Results

The results are summarized in Table I.

TABLE I

| Detergent in dilution buffer | $H_2O_2$ | Color Intensity (Average of Two Results) | |
|---|---|---|---|
| | | Without Ag | With Ag |
| SDS | − | 36 | 88 |
| SDS | + | 33 | 104 |
| Detergent I | − | 25 | 199 |
| Detergent I | + | 20 | 648 |
| None* | − | 23 | 497 |
| None** | − | 30 | 461 |

*prepared from GC solubilized with SDS
**prepared from GC solubilized with Detergent I Conclusions The assay response with GC diluted into 0.5% SDS is substantially less than when GC is diluted into detergent-free buffer and is not enhanced significantly by $H_2O_2$. Although the assay response with GC diluted into 0.5% Detergent I is greater than with SDS, it is still substantially less than when GC is diluted into detergent free buffer. After oxidation of detergent with $H_2O_2$ the assay response observed with 0.5% Detergent I is enhanced significantly and exceeds the response with detergent-free buffer. It is concluded that either detergent interferes with binding of the antigen to the filter and that only in the absence of strong detergents can binding occur. Hydrogen peroxide converts Detergent I to a weak detergent and permits binding and therefore a strong assay response.

Example III

This example illustrates the use of a chemically-modifiable thioether detergent in an assay for *Neisseria gonorrhoeae* (GC), and compares the effects of the detergent in its modified and unmodified forms on assay sensitivity. Solid phase-immobilized rabbit anti-GC polyclonal antibodies were used for specific capture of antigen and mouse anti-GC monoclonal antibodies for antigen detection.

Protocol
1. Sample Pretreatment

A. *N. gonorrhoeae* was solubilized ($1 \times 10^6$ cells/ml) in Dubecco's phosphate buffered saline (9 mM phosphate, pH 7.2, 150 mM NaCl) containing 1% Detergent I ($CH_3(CH_2)_5S(CH_2)_5OSO_3^-Na^+$), 0.1% Tween 20, and 2 mg/ml bovine serum albumin. The mixture was incubated for 15 minutes at room temperature.

B. $H_2O_2$ (30%) was added to 0.5 ml of the solubilized cells in a quantity sufficient to yield a final concentration of 1% and the mixture was incubated at room temperature for 15 minutes.

2. Assay Procedure

A. Aliquots (0.1 ml) of the solubilized cells before and after treatment with $H_2O_2$ were added to wells in a Suter-Butler coated microtiter plate (polystyrene coated in succession with biotinylated-KLH, streptavidin, and lastly with biotinylated rabbit anti-GC) and allowed to stand for 1 hour at 37° C. to promote the specific capture of solubilized antigen on the solid phase-immobilized rabbit anti-GC antibodies.

B. The samples were removed from the wells and the wells were subsequently washed four times with Dubecco's PBS containing 0.1% Tween-20. The wells were filled to capacity during each wash cycle.

C. The wells were next incubated for 1 hour at 37° C. with 0.10 ml mouse anti-GC monoclonal antibody (MAb 4G5) at 2 μg/ml in standard diluent (50% fetal calf serum, 0.1% Tween 20, 50% Dubellco's PBS).

D. The solutions were removed from the wells and the wells were subsequently washed four times as indicated above in step B.

E. The wells were next incubated for 1 hour at 37° C. with 0.1 ml HRP-labeled goat anti-mouse IgG (0.12 μg/ml) in standard diluent.

F. The solutions were removed from the wells and the wells were subsequently washed four times as indicated above in step B.

G. The wells were then incubated for 30 minutes at room temperature with 0.10 ml of a solution of 0.83 mM 3,3,5, 5'-tetramethyl benzidine-dihydrochloride, 1 mM EDTA and 4 mM urea peroxide in 50 mM citrate, pH 3.8.

H. Reactions were stopped by the addition of 0.1 ml in $H_2SO_4$ to each well.

I. Color intensity in each well was determined by measuring absorbance at 450 nm.

| Results | |
|---|---|
| Solubilization Treatment | Absorbance at 450 nm* |
| $H_2O_2$ (1%) | 1.81 |
| none | 0.18 |

*Average of values obtained in duplicate assays. No Ag controls were run; absorbance values observed for such assays are generally in the range of 0.1 to 0.2.

Conclusion

The above data demonstrate that the assay interference associated with the presence of Detergent I in its native form is reduced substantially by treatment with $H_2O_2$.

Example IV

This example illustrates the use of a chemically-modifiable thioether detergent in the assay for *Chlamydia trachomatis* (CT), and compares the effects of the detergent in its modified and unmodified forms on assay sensitivity using glass fiber for non-specific capture of antigen and rabbit polyclonal antibodies for antigen detection.

Protocol
1. Sample Pretreatment

A. Several Chlamydia-negative clinical swab samples (specimen collection site:human female urogenital tract) were solubilized with 1.0 ml 0.1M acetate (pH 5.5) containing 1% Detergent I and incubating the mixtures at room temperature for 15 minutes.

B. The swabs were removed and the solutions were combined to yield a clinical sample pool.

C. Two aliquots (vol.=0.40 ml) of the clinical sample pool were combined with Chlamydia Elementary Bodies (EBs) that had been solubilized in 0.1M acetate, 0.1M NaCl, pH 4.6 containing 0.5% Detergent I as described for GC in Example II. Sufficient solubilized antigen was added to yield a final concentration equivalent to $1 \times 10^5$ EBs/ml. Controls consisted of the clinical sample pool alone without EBs added.

D. One aliquot was combined with sufficient $H_2O_2$ (30%) to yield a final concentration of 1%, and then incubated at room temperature for 15 minutes.

2. Assay Procedure

A. A portion of each aliquot (0.05 ml) was applied to separate glass fiber filters (1.0μ pore size) mounted on absorbent paper pads.

B. 0.1 ml standard diluent (50% fetal bovine serum, 15% glycerol, 34.9% 0.01M Tris, pH 7.5, and 0.1% Tween 20 was added to each glass fiber filter.

C. 0.05 ml 1% whole Rabbit Anti-CT antiserum (in standard diluent) was applied to each filter which was then allowed to stand at room temperature for 5 minutes.

D. 0.1 ml of the Standard Diluent was added to each filter.

E. 0.05 ml 1 μg/ml Horseradish peroxidaze (HRP)-labeled goat anti-rabbit IgG (Heavy plus light chains) in Standard Diluent was applied to each filter which was then allowed to stand at room temperature for 5 minutes.

F. Washing was then carried out by applying 0.1 ml Standard Diluent followed by 0.1 ml of citrate pH 5.5 to each filter.

H. 0.05 ml of a buffered solution of dicarboxidine and $H_2O_2$, pH 5.5, was applied and incubation was carried out at room temperature for 8 minutes.

I. Reactions were stopped by addition of 0.1M citrate, pH 5.5 (0.1 ml).

J. Color intensity was recorded at the reaction site.

| | Results | |
|---|---|---|
| | Color Intensity* | |
| Solubilization Treatment | + EBS | − EBS |
| $H_2O_2$ (1%) | 993 | 1 |
| none | 190 | 1 |

*arbitrary units

Conclusion

The above data demonstrate that the assay interference associated with the presence of Detergent I in its native form is reduced substantially by treatment with $H_2O_2$.

Example V

Preparation of: 7-Thia-tetradecan-5-ene-1-ol
($CH_3$—$(CH_2)_6$—S—CH=CH—$(CH_2)_4$—OH)

To 1.332 gr (10 mmol) of n-heptyl mercaptan and 981 mg (10 mmol) of 5-hexyn-1-ol dissolved in 25 ml of heptane under an argon atmosphere was added a few crystals of dibenzoyl peroxide. The reaction was stirred magnetically and heated to reflux for 18 hours. It was then cooled and poured into 25 ml of 10% sodium bicarbonate and extracted with 3×25 ml of ethyl acetate. The organic phases were combined and dried over sodium sulfate, filtered, and evaporated to yield a yellow oil. The oil was chromatographed on eight silica gel type GF preparative plates, using hexane-ethyl acetate (4:1) as developing solvent. Following removal of the band corresponding to product from the plates, the product was extracted from the silica with methanol, 684 mg (30% yield) of pure 7-thia-tetradecan-5-ene-1-ol was obtained as a pale yellow oil.

$^1$H NMR (ppm, $CDCl_3$): 0.82(t,3H,$CH_3$), 1.1–1.8(m,14H, —$CH_2$), 2.1(m,2H,—$CH_2$—C=C—), 2.6(t,2H,—$CH_2$S—), 3.62(t,2H,—$CH_2$OH), 5.38–6.0(m,2H,—CH=CH—).

Example VI

Preparation of: Sodium 7-thiatetradecan-5-ene-1-ol Sulfate
($CH_3$—$(CH_2)_6$—S—CH=CH—$(CH_2)_4$—$OSO_3$Na)

To a stirred solution of 1.40 gr (10.4 mmol) of 7-thia-tetradecan-5-ene-1-ol from the previous reaction in 10 ml of dry pyridine was added under an argon atmosphere 1.39 gr (10.4 mmol) of sulfur trioxide-trimethylamine complex. The reaction was heated to 50°–60° for 15 minutes, then stirred overnight at room temperature. The reaction was monitored by thin layer chromatography (50% hexane-ethyl acetate: silica gel GF plates: iodine visualization) to confirm formation of the new, polar product. All pyridine was evaporated from the reaction, the product was dissolved in 10 ml of water, and 10 ml of a freshly prepared solution of 1N sodium hydroxide was added dropwise with cooling. The colorless solution was frozen and lyophilized overnight; 1.66 gr (77% yield) of sodium 7-thia-tetradecan-5-ene-1-ol sulfate was obtained as a white powder.

$^1$H NMR(ppm,$D_2O$): 0.70(t,3H,$CH_3$), 0.9–1.8(br m,14H, —$CH_2$—), 1.98(m,2H,—$CH_2$—C=C—), 2.50(t,2H,—$CH_2$S—), 3.91(t,2H,—$CH_2OSO_3$Na), 5.30–5.95(m,2H,—CH=CH—).

Although the foregoing invention has been described in some detail by way of illustration and example for purposes of clarity and understanding, it will be obvious that certain changes and modifications may be practiced within the scope of the appended claims.

We claim:

1. A method for destroying the detergent properties of a detergent in an aqueous medium containing a biological antigen selected from the group consisting of poly(amino acids), polysaccharides, liposaccharides, glycoproteins, lipoproteins and ribonuclear proteins, said method comprising the step of contacting said medium with a modifying reagent whereby said detergent is chemically modified by nucleophilic cleavage, nucleophilic substitution, oxidation or reduction, to destroy its detergent properties, wherein said detergent is a compound having the structural formula L—P where L is a lipophilic portion having the structural formula Y—A—Z capable of modification by said modifying reagent, in which:

Y is alkyl, alkenyl, or alkynyl, having from 2 to 12 carbon atoms; or aralkyl, aralkenyl or aralkynyl, having from 7 to 12 carbon atoms;

A is a modifiable group selected from the group consisting of —S—; —Se—; —CHX—, —CH(X)CH=CH— wherein X is Cl, Br, or I: —O—CH=CH—; and —S—CH=CH—, said modifiable group being capable of being chemically modified by said modifying reagent; and Z is saturated or unsaturated alkylene having from 1 to 12 carbon atoms or saturated or unsaturated aralkylene having from 7 to 10 carbon atoms; and P is a polar portion.

2. The method of claim 1 wherein P is selected from the group consisting of $OSO_3H$, $SO_3H$, COOH, PO(OR)OH, and OPO(OR)OH, wherein R is H or lower alkyl.

3. The method of claim 2 wherein said detergent is $CH_3(CH_2)_n$—S—$(CH_2)_mOSO_3H$ or a salt thereof, wherein n is an integer of 1 to 6, and m is an integer of 4 to 11; and said modifying reagent is selected from the group consisting of hydrogen peroxide, peracetate, persulfate, and hypochlorite.

4. The method of claim 1 wherein said detergent is oxidized and said modifying reagent is a peroxide or a peracid.

5. The method of claim 4 wherein said peroxide is selected from the group consisting of a lower alkyl, acyl hydroperoxide, and $H_2O_2$.

6. The method of claim 4 wherein said peracid is perborate or persulfate.

7. The method of claim 1 wherein said detergent is oxidized and said modifying reagent is hypochlorite or hypobromite.

8. The method of claim 1 wherein said detergent is reduced and said modifying reagent is selected from the group consisting of a sulfite, a hyposulfite salt, and a mercaptan.

9. The method of claim 1 wherein said detergent is modified by nucleophilic cleavage and said modifying reagent is a nucleophile and said nucleophile is selected from the group consisting of a thiosulfate, a mercaptoacid, a thiourea, a hydroxylamine, a hydrazine, a hydrazide, and ammonia.

10. The method of claim 1 wherein A is CHX—CH=CH and said modifying reagent is an anion selected from the group of anions containing sulfur, oxygen, or nitrogen.

11. The method of claim 1 wherein said detergent is $CH_3(CH_2)_n-S-(CH_2)_mOSO_3H$ or a salt thereof, wherein n is an integer of 1 to 6, and m is an integer of 4 to 11.

12. The method of claim 11 wherein said detergent is selected from the group consisting of $CH_3(CH_2)_2-S-(CH_2)_{11}OSO_3H$, $CH_3(CH_2)_6-S-(CH_2)_6OSO_3H$, $CH_3(CH_2)_5-S-(CH_2)_5OSO_3H$, and $CH_3(CH_2)_4-S-(CH_2)_6OSO_3H$, or a salt of any of the foregoing; and said modifying reagent is selected from the group consisting of hydrogen peroxide, peracetate, persulfate, and hypochlorite.

* * * * *